United States Patent [19]
Gröning et al.

[11] Patent Number: 6,166,223
[45] Date of Patent: Dec. 26, 2000

[54] PROCESS FOR THE PREPARATION OF 2,4-DIMETHYLPYRROLE

[75] Inventors: Carsten Gröning, Mannheim; Reinhard Kemper, Heidelberg; Markus Frede, Eppelheim; Klaus Ebel, Lampertheim, all of Germany

[73] Assignee: BASF Aktiengesellschaft, Ludwigshafen, Germany

[21] Appl. No.: 09/459,722

[22] Filed: Dec. 13, 1999

[30] Foreign Application Priority Data

Dec. 17, 1998 [DE] Germany .............................. 198 58 360

[51] Int. Cl.$^7$ ................................................ C07D 207/323

[52] U.S. Cl. ............................................................ 548/564

[58] Field of Search ............................................... 548/564

[56] References Cited

PUBLICATIONS

Corwin et al., J. Am. Chem. Soc., 63, 1941, 1829–1834.
*Org. Synth. Coll.*, vol. II, 1943, 217–218.
*Org. Synth. Coll.*, vol. II, 1943, 202–204.

*Primary Examiner*—Joseph K. McKane
*Assistant Examiner*—Joseph Murray
*Attorney, Agent, or Firm*—Keil & Weinkauf

[57] ABSTRACT

A process for the preparation of 2,4-dimethylpyrrole is described in which a 2,4-dimethyl-3,5-bisalkoxycarbonylpyrrole is refluxed with from 10 to 30% strength aqueous alkali metal hydroxide solution until the solid has passed into solution, the reaction mixture is neutralized with acid and the mixture is refluxed further until decarboxylation is complete. The process makes it possible to work under significantly milder, less aggressive conditions than are known from the prior art.

8 Claims, No Drawings

PROCESS FOR THE PREPARATION OF 2,4-DIMETHYLPYRROLE

The invention relates to a process for the preparation of 2,4-dimethylpyrrole from 2,4-dimethyl-3,5-bisalkoxycarbonylpyrrole by hydrolysis and decarboxylation.

The synthesis of 2,4-dimethyl-3,5-bisalkoxycarbonylpyrrole is described, for example, in Org. Synthesis, Coll. Vol. II, 202–204 (1943). It is preferably carried out in accordance with the process described in Patent Application 198 58 352.4 (NAE 19980438), which was filed at the same time, by nitrosating an acetoacetic alkyl ester, hydrogenating the 2-nitroso compound to give the amine with hydrogen in the presence of a noble metal catalyst, and condensing the amino compound with unsubstituted acetoacetic ester to give the pyrrole derivative.

The hydrolysis of 2,4-dimethyl-3,5-bisethoxycarbonylpyrrole and the subsequent decarboxylation of the dicarboxylic acid is described in Org. Synth., Coll. Vol. II, page 217 218 (1943) with a yield of from 57 to 63%. There, the ester is hydrolyzed with concentrated (64%) potassium hydroxide solution over the course of from 2 to 3 hours at 130° C. The decarboxylation is then carried out by heating the reaction mixture to from 160 to 200° C. The disadvantage of this process is that, at the required high temperatures, only expensive nickel steels are resistant toward the hydroxide solution.

Higher yields (about 95%) are given by Corvin et al in J. Am. Chem. Soc. 63, 1829–1834 (1941), according to which highly concentrated potassium hydroxide solutions or melts are reacted with the dicarboxylic diethyl ester at 160° C. under pressure for from 4 to 5 hours. Here too, very aggressive reaction mixtures are required.

It is an object of the present invention to propose a process for the preparation of 2,4-dimethylpyrrole from 2,4-dimethyl-3,5-bisalkoxycarbonylpyrrole which gives the product in good yield and can be carried out under conditions which are milder than those described in the prior art.

We have found that this object is achieved by a process for the preparation of 2,4-dimethylpyrrole in which a 2,4-dimethyl-3,5-bisalkoxycarbonylpyrrole is hydrolyzed with a strong alkali to give the dicarboxylic acid, and the dicarboxylic acid is thermally decarboxylated.

The process according to the invention comprises refluxing the dicarboxylic alkyl ester with from 10 to 30% strength aqueous alkali metal hydroxide solution, preferably sodium hydroxide solution, until the solid has passed into solution, neutralizing the reaction mixture with acid, and refluxing the mixture further until decarboxylation is complete, i.e. until the evolution of gas has stopped.

In the first stage, the hydrolysis of the ester groups is preferably carried out at atmospheric pressure and using a stoichiometric excess of alkali. The reflux temperature begins then firstly above the boiling point of the corresponding alcohol and increases to values above 100° C. with removal of the latter from the equilibrium depending on the concentration of the alkali metal hydroxide solution. Generally, the hydrolysis takes place over the course of from 5 to 15 hours. The decarboxylation, at least of the first carboxyl group, also starts to take place under these conditions. Thus, from 90° C. or slightly above, gas starts to evolve vigorously. The resulting alcohol can advantageously be distilled off under the process conditions. If the reaction has subsided and the substance used has dissolved, the solution, advantageously after brief cooling to avoid vigorous evolution of heat, is neutralized with acid, advantageously a nonvolatile strong mineral acid, for example sulfuric acid or phosphoric acid. The mixture is then refluxed further, and the 2,4-dimethylpyrrole passes over together with water and can be separated off therefrom. This second decarboxylation stage can also be carried out under pressure, for example under the autogenous pressure of the mixture of about 10 bar at temperatures in the range from about 130 to 145° C. Carrying out the process under atmospheric pressure and distilling off the reaction products is generally preferred.

The dialkyl ester used as starting material can have alkyl groups having from 1 to 4 carbon atoms. In this connection, preference is given to methyl and ethyl esters since they are particularly reactive, and the resulting alcohols can be separated off more easily.

If the dialkyl ester is prepared by the process of the above-mentioned parallel application by nitrosation, hydrogenation and condensation from the acetoacetic alkyl ester, the hydrolysis and decarboxylation according to the present invention can also be carried out with the crude product which is obtained after catalytic hydrogenation to give the amine and condensation to give the dimethylbisalkoxycarbonyl-pyrrole and still contains the catalyst. After the ester hydrolysis stage, the catalyst can be separated off particularly easily by filtration.

The process according to the invention gives the desired 2,4-dimethylpyrrole in high yield without the need to use particularly alkali-resistant reaction vessels and apparatuses. Some of the by-products can be returned to the reaction zone, and some can be disposed off in a simple, environmentally friendly manner.

The examples below illustrate individual advantageous embodiments of the process according to the invention. Unless stated otherwise, parts and percentages are in units by weight.

EXAMPLE 1

399 g (1.89 mol) of 2,4-dimethyl-3,5-bismethoxycarbonylpyrrole, which had been obtained by hydrogenation of methyl 2-nitrosoacetoacetate to give the 2-amino compound and condensation with methyl acetoacetate and still contained about 4 g of catalyst material based on palladium/activated carbon, were stirred in 1250 g of 20% strength sodium hydroxide solution (6.25 mol of NaOH) and refluxed for 10 hours. The organic solid passes into solution during this process. The catalyst residue was then filtered off, and the dark filtrate was adjusted to pH 7 using 284 g of 95% strength sulfuric acid and then heated for 10 hours at from 135 to 140° C. under the autogenous pressure of the mixture which was established (9 to 10 bar).

Cooling gave a three-phase mixture: a liquid upper organic, product-containing phase, a lower aqueous phase and a solid as sediment. The solid (207 g) consisted predominantly of sodium sulfate and sodium carbonate and was filtered off.

The organic phase was separated off, and the aqueous phase was extracted with the same volume of ethyl acetate. The organic phases were combined and dried over sodium sulfate, and the ethyl acetate was distilled off. This gave 149.8 g of product, which comprised 84.1% of 2,4-dimethylpyrrole. This corresponded to a yield of 70%, based on 2,4-dimethyl-3,5-bismethoxycarbonylpyrrole.

EXAMPLE 2

420 g (2.0 mol) of 2,4-dimethyl-3,5-bismethoxycarbonylpyrrole were suspended in 1200 g of 20% strength sodium hydroxide solution, and the mixture was heated. The solid gradually passed into solution during this process. At 92° C. gas had started to evolve vigorously; some of the dicarboxylic acid was decarboxylated in the process. The methanol formed during the hydrolysis was distilled off continuously until essentially only water was passing over. The mixture which remained was then neutralized with 250 g of 50% strength sulfuric acid (pH about 7.5) and heated to boiling at the reflux condenser with water separator. The 2,4-dimethylpyrrole separated out as a yellow upper phase over the course of a few hours. The aqueous phase was continuously recycled into the boiling mixture. A total of 152.5 g of organic phase was obtained. This comprised 8.1% of water, the remainder consisted of 99.1% of 2,4-dimethylpyrrole, determined as area percentages by gas chromatography using a flame ionization detector. This corresponded to 138.9 g of 2,4-dimethylpyrrole (73% of theory).

We claim:

1. A process for the preparation of 2,4-dimethylpyrrole, wherein a 2,4-dimethyl-3,5-bisalkoxycarbonylpyrrole is hydrolyzed with a strong alkali to give the dicarboxylic acid, and the dicarboxylic acid is thermally decarboxylated, which comprises refluxing the dicarboxylic alkyl ester with from 10 to 30% strength aqueous alkali metal hydroxide solution until the solid has passed into solution, neutralizing the reaction mixture with acid, and refluxing the mixture further until decarboxylation is complete.

2. A process as claimed in claim 1, wherein the alkali metal hydroxide solution is sodium hydroxide solution.

3. A process as claimed in claim 1, wherein the hydroxide solution is neutralized using a strong nonvolatile mineral acid.

4. A process as claimed in claim 1, wherein the 2,4-dimethyl-3,5-alkoxycarbonylpyrrole has from 1 to 4 carbon atoms in the alkoxy group.

5. A process as claimed in claim 1, wherein the dicarboxylic alkyl ester is refluxed for the hydrolysis with alkali metal hydroxide solution for from 5 to 15 hours.

6. A process as claimed in claim 1, wherein the hydrolysis product is refluxed for the decarboxylation at from 130 to 145° C. under pressure.

7. A process as claimed in claim 1, wherein the hydrolysis product is refluxed under atmospheric pressure for the decarboxylation, and the 2,4-dimethylpyrrole which passes over with the water vapor is continuously separated off from the equilibrium.

8. A process as claimed in claim 1, wherein, for the hydrolysis, an excess of strong alkali is used.

* * * * *